United States Patent [19]
Jaatinen et al.

[11] Patent Number: 5,712,301
[45] Date of Patent: Jan. 27, 1998

[54] USE OF DEXMEDETOMIDINE FOR TREATING ETHANOL-INDUCED NEURODEGENERATION

[75] Inventors: Pia Helena Jaatinen, Tampere; Esa Henrik Heinonen, Turku; Antti Lauri Juhani Hervonen, Tampere; Lauri Sakari Nieminen, Lieto, all of Finland

[73] Assignee: Orion-yhtymä Oy, Espoo, Finland

[21] Appl. No.: 602,745

[22] PCT Filed: Aug. 24, 1994

[86] PCT No.: PCT/FI94/00371

§ 371 Date: Apr. 19, 1996

§ 102(e) Date: Apr. 19, 1996

[87] PCT Pub. No.: WO95/05820

PCT Pub. Date: Mar. 2, 1995

[30] Foreign Application Priority Data

Aug. 25, 1993 [GB] United Kingdom .................. 9317636

[51] Int. Cl.$^6$ ................................................ A61K 31/415
[52] U.S. Cl. ............................................................. 514/396
[58] Field of Search ............................................... 514/396

[56] References Cited

FOREIGN PATENT DOCUMENTS

| 30272/89 | 8/1989 | Australia . |
| 0 300 652 A1 | 1/1989 | European Pat. Off. . |

OTHER PUBLICATIONS

Bischoff, P. et al., Alpha$_2$-Agonisten in Anästhesie and Intensivmedizin, *Anästhesiol. Intensivmed. Notfallmed. Schmerzther* 28:2–12, Feb. 1993.

Charness, M.E., Brian Lesions in Alcoholics, *Alcoholism: Clinical and Experimental Research* 17:2–11, Jan./Feb. 1993.

CAS Database Abstract 110:16790t for Durcan, M.J. et al., Interactions of Alpha$_2$–Adrenoceptor Antagonists with Medetomidine and with Ethanol in a Holeboard Test, *Neuropharmacology* 28(3):275–281 (1989).

Durcan, M.J. et al., Interactions of Alpha$_2$–Adrenoceptor Antagonists With Medetomidine and With Ethanol in a Holeboard Test, *Neuropharmacology* 28:275–281, 1989.

Hillbom, M. et al., Ethanol Intoxication: A Risk Factor for Ischemic Brain Infarcation, *Stroke* 14:694–699, Sep./Oct. 1983.

Hoffman, W.E. et al., Dexmedetomidine Improves Neurologic Outcome from Incomplete Ischemia in the Rat. Reversal by the $\alpha_2$–Adrenergic Antagonist Atipamezole, *Anesthesiology* 75:328–332, Aug. 1991.

Lishman, W.A. et al., Brain damage in Alcoholism: Current Concepts, *Acta Med. Scand. Supp.* 717:5–17, 1987.

Maier, C. et al., Neuroprotection by the $\alpha_2$–Adrenoreceptor Agonist Dexmedetomidine in a Focal Model of Cerebral Ischemia, *Anesthesiology* 79:306–312, Aug. 1993.

Mandybur, T.I. et al., The Effects of Chronic Alcoholism on Development of Ischemic Cerebral Infarcts Following Unilateral Carotid Artery Ligation in Gerbils, *Alcoholism: Clinical and Experimental Research* 7:357–361, Fall 1983.

*Primary Examiner*—Raymond Henley, III
*Attorney, Agent, or Firm*—Sterne, Kessler, Goldstein & Fox P.L.L.C.

[57] ABSTRACT

The present invention involves the prevention of ethanol-induced neurodegeneration through the administration to a subject before, during and/or after ethanol consumption an effective amount of dexmedetomidine of a pharmaceutically acceptable salt thereof.

26 Claims, 2 Drawing Sheets

USE OF DEXMEDETOMIDINE FOR TREATING ETHANOL-INDUCED NEURODEGENERATION

This is a 371 of PCT/FI94/00371 filed Aug. 24, 1994.

This invention relates to prevention of neurodegeneration induced by ethanol consumption.

Ethanol exposure causes degeneration of the nervous system. Neurodegeneration occurs during ethanol exposure and continues even long after cessation of ethanol intake (Cadete-Liete et al. Neurosci Lett 86: 45–50, 1988). Neuropathological changes induced by ethanol consumption are associated with the impairment of neuronal functions e.g. cognitive dysfunctions. To our knowledge no succesfull intervention to prevent loss of normal neuronal structure and functional activity due to alcohol exposure has been reported before.

Dexmedetomidine (dextro-4-{1(2,3-dimethylphenyl)ethyl}-1H-imidazole) is a relatively new, selective and potent $\alpha$2-adrenoreceptor agonist, which has been disclosed in European patent no. 300652. EP 331374 and EP 424059 disclose dexmedetomidine in perioperative and epidural use, respectively. EP 413487 discloses transdermal delivery of dexmedetomidine and EP 437030 discloses the use of dexmedetomidine in glaucoma.

We have now found that dexmedetomidine is also effective in preventing ethanol-induced neurodegeneration. Thus the present invention provides dexmedetomidine or a pharmaceutically acceptable acid addition salt thereof for use in the prevention of neurodegeneration induced by ethanol consumption, and for use in the manufacture of a pharmaceutical preparation for the prevention of neurodegeneration induced by ethanol consumption.

Dexmedetomidine or a pharmaceutically acceptable acid addition salt thereof is administered before and/or during and/or after the ethanol consumption. One example of the use of the present invention is administration of dexmedetomidine during and after ethanol intoxication. Use of the present invention is not, however, limited to this particular case. The drug is preferably administered perorally, transmucosally, intravenously, intramuscularly or transdermally. The preferable daily dose is 0.1–5.0 μg/kg i.v. or 5–50 μg/kg per os.

EXPERIMENTAL

Rats to which ethanol is given show neuropathological changes in the peripheral symphathetic neurons of the superior cervical ganglion. A loss of neurotransmitter synthetic capacity (reflected by tyrosine hydroxylase immunoreactivity, TH-IR) was observed in several neurons of the ethanol-exposed rats, while another population of neurons showed signs of abnormally high catecholamine turnover. When given perorally during ethanol exposure, dexmedetomidine significantly reduced these changes. The ethanol+dexmedetomide treated ganglia exhibited homogenous TH-IR and catecholamine fluorescence intensities, comparable to those seen in the control ganglia. Dexmedetomidine also inhibited the occurence of vacuolated neurons, which are considered to be an indication of neuronal degeneration. These results indicate that dexmedetomidine has a neuroprotective role in ethanol exposure.

PROCEDURES

Fifteen 4-month old male Wistar rats were used in the study. The rats were housed individually under standard conditions (+21°±1° C., lights on between 8 am and 9 pm) and were carefully habituated to handling before the experiment was started.

Dexmedetomidine hydrochloride (Orion Corporation FARMOS, Batch no. ST0531) was dissolved in distilled water, 100 μg/ml, and was given to the treatment group (EtOH+dex) through an intragastric feeding tube with ethanol feed twice a day. Dexmedetomidine volume was 1 ml/kg.

The rats were divided into three groups (five animals in each group): one receiving ethanol (EtOH), one ethanol and dexmedetomidine (EtOH+dex) and one isocaloric sucrose (control). To ensure a high and accurate dosage of ethanol, intragastric intubation of 25% ethanol+5% sucrose was used three times a day (8 am, 2 pm, 8 pm). The daily dose of ethanol was gradually increased to 10 g/kg as absolute alcohol. The duration of the ethanol exposure was 10 days. To avoid deaths during the course of the experiment, severely intoxicated animals were given reduced doses of ethanol; rats having lost their righting reflex were intubated with isocaloric sucrose only. The ethanol-exposed rats had free access to standard laboratory rat food and tap water. The EtOH+dex group was exposed to ethanol in the same manner, and received dexmedetomidine 100 μg/kg p.os. with the ethanol intubations at 8 am and 8 pm. The control rats were intubated with similar amounts of isocaloric sucrose three times a day and were given food according to the consumption of the EtOH-group (pair-feeding), to allow for the possible impact of malnutrition in the pathology observed.

The rats were killed by decapitation under light ether anesthesia between 10 am and 12 am, i.e. 2–4 hours after the last ethanol/sucrose intubation. The superior cervical symphathetic ganglia (SCG) were rapidly prepared and frozen in liquid nitrogen. After storing in liquid nitrogen, the ganglia were processed for histochemical detection of catecholamines by the standardized formaldehyde-induced fluorescence (FIF) method (Eränkö, Roy Microsc Soc 87:259–276, 1967) as described in detail previously (Jaatinen et al., Mech Ageing Dev 63: 193–205, 1992). Every tenth section (thickness 10 μm) was viewed through an Olympus Vanox-T fluorescence microscope equipped with a special filter combination for the detection of monoamines (filter block "V", excitation light wave length 395 to 415 nm, emission light 455 nm and up). Two randomly selected sections from the middle part of the ganglion were processed for pseudocolor video prints by a Mitsubishi CP 100E video printer, to provide an objective image of the neuronal FIF-intensity. Tyrosine hydroxylase immunoreactivity (TH-IR), reflecting the amount of the rate limiting enzyme of catecholamine biosynthesis, was demonstrated by using the peroxidase-antiperoxidase (PAP) technique of Sternberger (Immunocytochemistry, Prentice Hall, Englewood Cliffs, N.J., 1974) on sections previously studied by fluorescence microscopy. The dilution of the TH-antiserum (Eugene Tech. International) was 1:1000 and the incubation time was 24 hours at +4° C. Goat anti-rabbit serum (1:80) and PAP (1:80) incubations were carried out for 30 minutes at room temperature. Diaminobenzidine was used as chromogen.

The proportions of TH-positive and TH-negative neurons and of vacuolated neurons were measured from two randomly selected TH-IR sections at least 100 μm apart in the middle part of the superior cervical sympathetic ganglia. The morphometric measurements were carried out with a Hamamatsu ARGUS-10 image processor (Hamamatsu Photonics, Japan).

The results are expressed as mean ±SEM. The analysis of variance was used to identify overall effects (treatment—i.e.

ethanol, ethanol and dexmedetomidine or no treatment—as a factor). The effects of the treatments were further analysed by Student's two way t-test. A tail probability of less than 0.05 was considered to be indicative of a statistically significant difference.

RESULTS

Formaldehyde-induced catecholamine histofluorescence (FIF) revealed remarkable differences between the groups in the amount of noradrenaline in the SCG (see FIG. 1a,c,f). The overall level of FIF-intensity was markedly higher in the EtOH ganglia (FIG. 1c) than in the control (FIG. 1a) or EtOH+dex ganglia (FIG. 1f). FIF and TH-intensities varied largely from neuron to neuron in the EtOH SCG (FIG. 1c,d), while FIF and TH-IR intensities in the EtOH+dex ganglia (FIG. 1e,f) were rather homogenous and comparable to those in control ganglia (FIG. 1a,b). The strongly fluorescent neurons in the EtOH ganglia also had strong TH-IR, suggesting a high catecholamine turnover in these cells (see FIG. 2a,b). On the other hand, a substantial population of neurons in the EtOH ganglia has neither TH-IR nor noradrenaline fluorescence which indicates a loss of catecholamine synthetic capability in these neurons (FIG. 2a,b).

The ganglia of the ethanol-treated rats showed a remarkable population of vacuolated neurons (see FIG. 2c,d) while the ganglia of the EtOH+dex or the control animals had approximately one vacuolated neuron per section. The appearance of vacuolated neurons in the ganglia of the sympathetic trunk has been regarded as a sign of neurosecretion or degeneration (Partanen et al., Cell Tissue Res 199:373–386, 1979; Nouhouayi et al., Z Microsc Anat Forsch 93: 1025–1037,1979; Mikulajova et al., Bratisl Lek Listy 90: 793–800, 1989). Increased stimulation of the SCG-neurons was apparent; the vacuolated neurons usually showed signs of high catecholamine turnover judging from a high TH-IR and FIF-intensity. In a follow-up study (Jaatinen et al., Ethanol-induced vacuolation in rat peripheral nervous system. J Autonomic Nervous System 1993, in press) where the rats were allowed to survive up to 4 weeks after the ethanol exposure part of the vacuolated neurons lost their TH-IR and FIF and showed degenerative changes in electron microscopy. The vacuolation can represent a particular response of a population of sympathetic neurons to excessive stimulation which may ultimately result in loss of functional abilities and cellular death.

ANOVA (analysis of variance) revealed a significant difference between the groups in the proportion of vacuolated neurons ($F(2,27)=17.18$, $p=0.0000$) and in the proportion of TH-negative neurons ($F(2,27)=39.89$, $p=0.0000$).

Dexmedetomidine significantly reduced the morphometric, neuropathologic changes observed in the SCG after the ethanol exposure (see table 1 below). The proportion of TH-negative neurons was approximately twice (mean 11.46 vs. 5.72%) in the EtOH ganglia compared to the control ganglia, whereas the EtOH+dex ganglia did not differ from the controls in this respect. Similarily the proportion of vacuolated neurons was significantly higher (6 to 7-fold) in the EtOH group than in the EtOH+dex group or in the controls.

TABLE I

Morphometric data on the superior cervical sympathetic ganglion (mean ± SEM)

| Group | Vacuolated neurons (%) | TH-negative neurons (%) |
|---|---|---|
| Control (n = 5) | 0.11 ± 0.05 | 5.72 ± 0.50 |
| EtOH (n = 5) | 0.79 ± 0.15* | 11.46 ± 0.39* |
| EtOH + dex (n = 5) | 0.14 ± 0.04 | 6.09 ± 0.61 |

*significantly different from the control and dexmedetomidine-treated groups, $p < 0.001$

BRIEF DESCRIPTION OF THE DRAWINGS

The accompanying drawings (FIG. 1a,c,f) show pseudocolor videoprints representing the formaldehyde-induced catecholamine histofluorescence (FIF) in the superior cervical sympathetic ganglia of control, (FIG. 1a) ethanol-treated (EtOH) (FIG. 1c) and ethanol+dexmedetomidine-treated (EtOH+dex) (FIG. 1f) rats.

Figure 1A:
FIG. 1b,d,e, show tyrosine hydroxylase immunoreactivity (TH-IR) of the same ganglia. Note the extremely bright catecholamine fluorescence in the EtOH ganglion (FIG. 1c); FIF-intensity in the EtOH+dex ganglion (FIG. 1f) is comparable to the control ganglion (FIG 1a). TH-IR is relatively homogeneous in the EtOH+dex (FIG. 1c) and the control ganglia (FIG. 1b), whereas TH-IR varies largely from neuron to neuron in the EtOH ganglion (FIG. 1d).
Figure 1B:
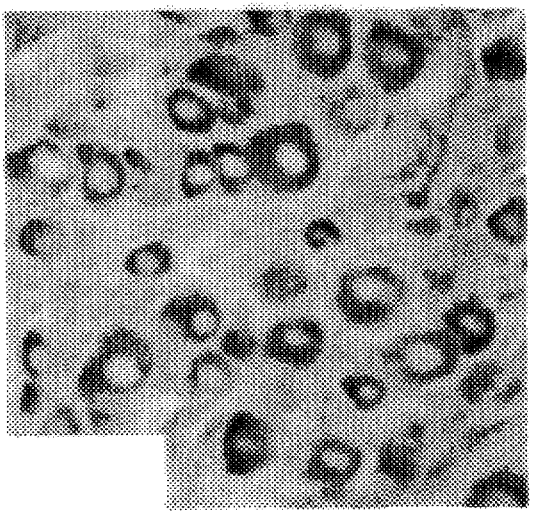
Figure 1C:
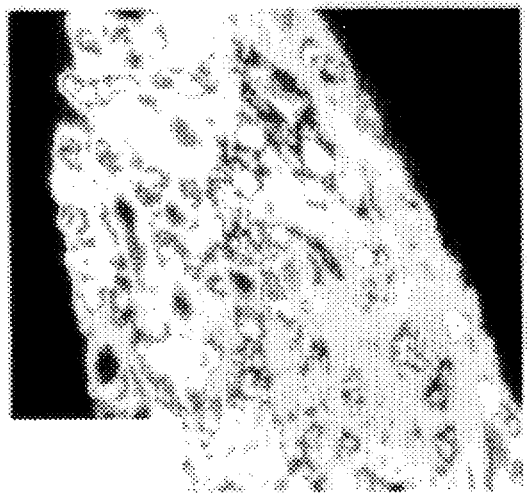
Figure 1D:
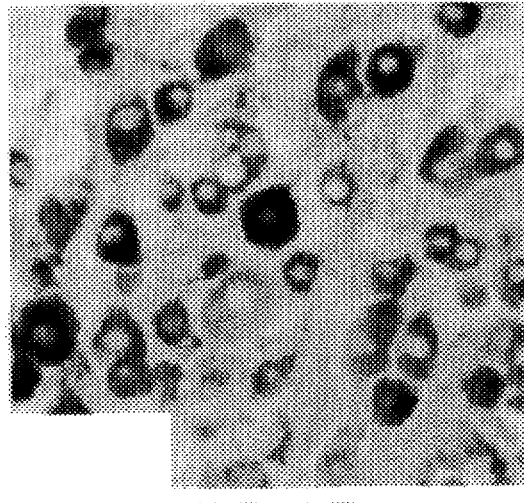
Figure 1F:
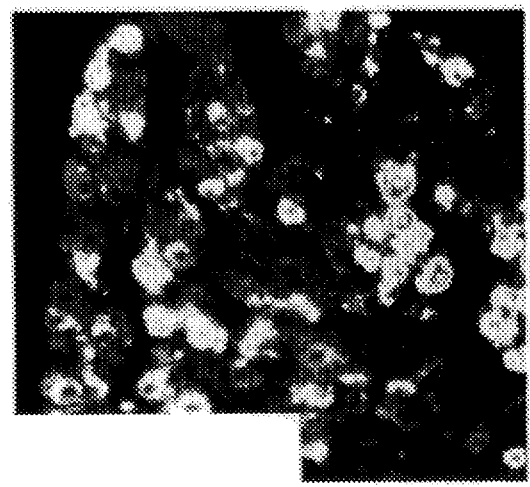
Figure 1E:
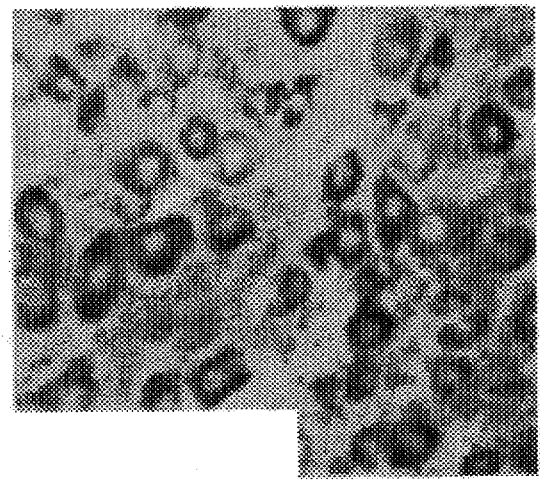
Figure 2A:
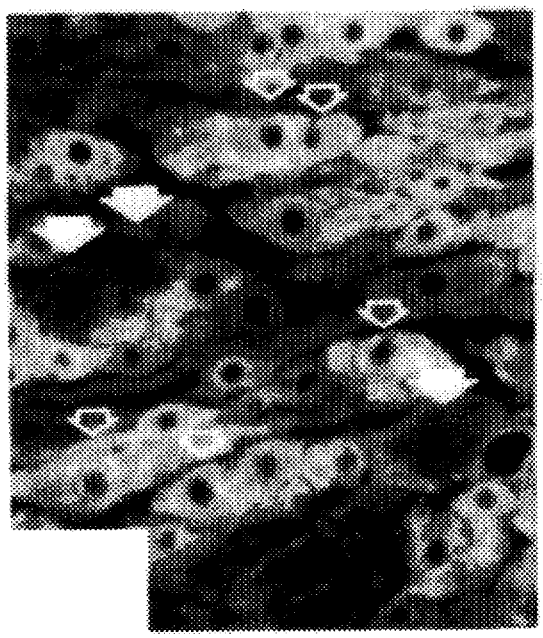
(FIG. 2a,b). The strongly fluorescent neurons in the EtOH ganglia usually have strong TH-IR, suggesting a high catecholamine turnover in these cells (open arrows). A population of neurons (mostly large ones) in the EtOH ganglia have neither TH-IR nor noradrenaline fluorescence, which indicates a loss of catechloamine synthetic capability in these neurons (solid arrows) (FIG. 2c,d). A characteristic finding in the EtOH ganglia was the appearance of vacuolated neurons (arrowheads). Most of the vacuolated neurons have high FIF and TH-IR intensities, suggesting high functional activity. The cytoplasmic vacuolation probably reflects a specific response of the neurons to eccessive stimulation.
Figure 2B:
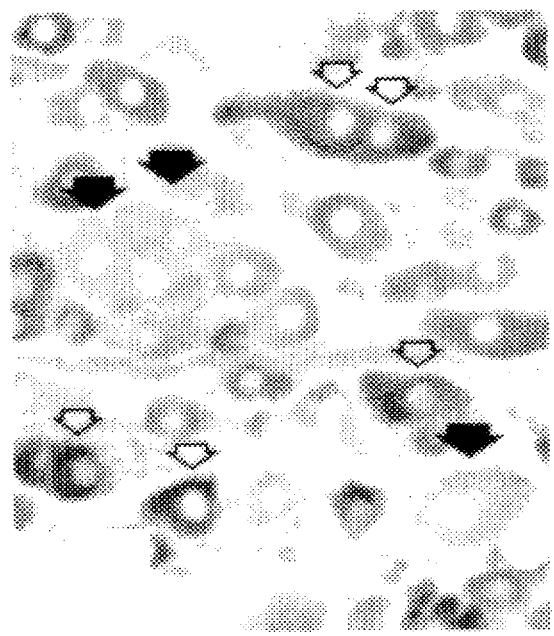
FIG. 2 left shows formaldehyde-induced catecholamine fluorescence in an EtOH ganglion, and right shows the same sections after immunohistochemical demonstration of tyrosine hydroxylase, the rate limiting enzyme of catecholamine synthesis.
Figure 2C:
Figure 2D:
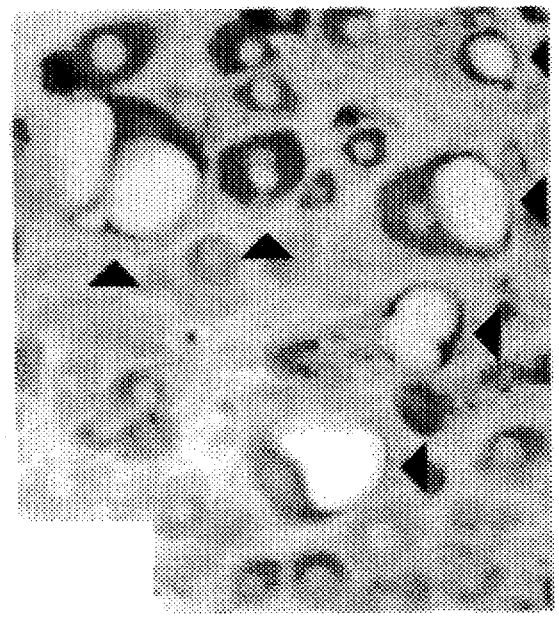

We claim:

1. A method of prevention of neurodegeneration in a subject induced by ethanol consumption comprising administration to said subject of an amount of dexmedetomidine or a pharmaceutically acceptable acid addition salt thereof effective to prevent such neurodegeneration.

2. A method according to claim 1 comprising administration of an effective amount of dexmedetomidine or a pharmaceutically acceptable acid addition salt thereof before and/or during and/or after ethanol consumption.

3. The method of claim 1, wherein said subject is administered said dexmedetomidine.

4. The method of claim 1, wherein said subject is administered said pharmaceutically acceptable acid addition salt of dexmedetomidine.

5. The method of claim 2, wherein said subject is administered said dexmedetomidine.

6. The method of claim 5, wherein said dexmedetomidine is administered before said ethanol consumption.

7. The method of claim 5, wherein said dexmedetomidine is administered during said ethanol consumption.

8. The method of claim 5, wherein said dexmedetomidine is administered after said ethanol consumption.

9. The method of claim 7, wherein said dexmedetomidine is administered before and during said ethanol consumption.

10. The method of claim 8, wherein said dexmedetomidine is administered before and after said ethanol consumption.

11. The method of claim 8, wherein said dexmedetomidine is administered during and after said ethanol consumption.

12. The method of claim 8, wherein said dexmedetomidine is administered before, during and after said ethanol consumption.

13. The method of claim 2, wherein said subject is administered said pharmaceutically acceptable acid addition salt of dexmedetomidine.

14. The method of claim 13, wherein said pharmaceutically acceptable acid addition salt of dexmedetomidine is administered before said ethanol consumption.

15. The method of claim 13, wherein said pharmaceutically acceptable acid addition salt of dexmedetomidine is administered during said ethanol consumption.

16. The method of claim 13, wherein said pharmaceutically acceptable acid addition salt of dexmedetomidine is administered after said ethanol consumption.

17. The method of claim 15, wherein said pharmaceutically acceptable acid addition salt of dexmedetomidine is administered before and during said ethanol consumption.

18. The method of claim 16, wherein said pharmaceutically acceptable acid addition salt of dexmedetomidine is administered before and after said ethanol consumption.

19. The method of claim 16, wherein said pharmaceutically acceptable acid addition salt of dexmedetomidine is administered during and after said ethanol consumption.

20. The method of claim 16, wherein said pharmaceutically acceptable acid addition salt of dexmedetomidine is administered before, during and after said ethanol consumption.

21. The method according to any one of claims 1 or 2, wherein said dexmedetomidine or said pharmaceutically acceptable acid addition salt thereof is administered perorally, transmucosally, intravenously, intramuscularly or transdermally.

22. The method of claim 21, wherein said dexmedetomidine or pharmaceutically acceptable acid addition salt thereof is administered perorally.

23. The method of claim 21, wherein said dexmedetomidine or pharmaceutically acceptable acid addition salt thereof is administered transmucosally.

24. The method of claim 21, wherein said dexmedetomidine or pharmaceutically acceptable acid addition salt thereof is administered intravenously.

25. The method of claim 21, wherein said dexmedetomidine or pharmaceutically acceptable acid addition salt thereof is administered intramuscularly.

26. The method of claim 21, wherein said dexmedetomidine or pharmaceutically acceptable acid addition salt thereof is administered transdermally.

* * * * *